(12) United States Patent
Fischbach et al.

(10) Patent No.: US 11,504,189 B2
(45) Date of Patent: Nov. 22, 2022

(54) HYBRID APPROACH TO DISTORTION DETECTION

(71) Applicant: St. Jude Medical International Holding S.à r.l., Luxembourg (LU)

(72) Inventors: Adam C. Fischbach, Inver Grove Heights, MN (US); Scott Meyerson, Ham Lake, MN (US)

(73) Assignee: ST JUDE MEDICAL INTERNATIONAL HOLDING S.À R.L., Luxembourg (LU)

(*) Notice: Subject to any disclaimer, the term of this patent is extended or adjusted under 35 U.S.C. 154(b) by 147 days.

(21) Appl. No.: 17/139,877

(22) Filed: Dec. 31, 2020

(65) Prior Publication Data

US 2021/0244484 A1 Aug. 12, 2021

Related U.S. Application Data

(60) Provisional application No. 62/971,039, filed on Feb. 6, 2020.

(51) Int. Cl.
*A61B 5/00* (2006.01)
*A61B 34/20* (2016.01)
*A61B 5/06* (2006.01)

(52) U.S. Cl.
CPC ............ *A61B 34/20* (2016.02); *A61B 5/062* (2013.01); *A61B 5/063* (2013.01); *A61B 5/068* (2013.01)

(58) Field of Classification Search
CPC .. A61B 2017/00243; A61B 2034/2051; A61B 2034/2053; A61B 2034/2072; A61B 34/20; A61B 5/062; A61B 5/063; A61B 5/068; A61B 5/367; A61B 5/7207
See application file for complete search history.

(56) References Cited

U.S. PATENT DOCUMENTS

| | | | |
|---|---|---|---|
| 6,233,476 B1 | 5/2001 | Strommer et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,885,707 B2 | 2/2011 | Hauck | |

(Continued)

FOREIGN PATENT DOCUMENTS

WO 2014/141113 A2 9/2014

*Primary Examiner* — Mark D Remaly
(74) *Attorney, Agent, or Firm* — Billion & Armitage

(57) ABSTRACT

A system for differentiating between magnetic field distortion and physical movement in a hybrid magnetic and impedance tracking system can comprise a first drive patch and a second drive patch configured to generate an electrical field within the body for locating an electrode on the medical device, a magnetic localization system configured to generate a magnetic field, a magnetic sensor configured to receive signals from the magnetic localization system, and an electronic control unit configured to receive location data from the impedance localization system and magnetic sensor location data from the magnetic localization system. The electronic control circuit can be configured to detect a location change of the magnetic sensor and use the drive patch location data and magnetic sensor location data to determine whether the detected location change of the magnetic sensor is caused by a magnetic field distortion or a physical movement of the magnetic sensor.

20 Claims, 9 Drawing Sheets

(56) References Cited

U.S. PATENT DOCUMENTS

| | | |
|---|---|---|
| 9,326,702 B2 | 5/2016 | Eichler et al. |
| 9,901,303 B2 | 2/2018 | Olson |
| 10,758,137 B2 | 9/2020 | Deno et al. |
| 10,918,307 B2 | 2/2021 | Olson et al. |
| 2007/0060833 A1 | 3/2007 | Hauck |
| 2012/0172702 A1 | 7/2012 | Koyrakh et al. |
| 2017/0209072 A1 | 7/2017 | Oren et al. |
| 2018/0296111 A1 | 10/2018 | Deno et al. |

HYBRID APPROACH TO DISTORTION DETECTION

CROSS-REFERENCE TO RELATED APPLICATIONS

This application claims the benefit of U.S. provisional application No. 62/971,039, filed 6 Feb. 2020, which is hereby incorporated by reference in its entirety as though fully set forth herein.

BACKGROUND a. Field

The present disclosure relates generally to the localization of medical instruments within a human body. More specifically, the instant disclosure relates to detecting and differentiating between magnetic field distortions and positional change distortions within hybrid magnetic tracking and impedance-based tracking systems.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which can be used for diagnosis, mapping, ablation, or other treatments. Precise positioning of the catheters and clinician knowledge of the precise location within the body of the patient is desirable for improved procedure success rates.

To position a catheter within the body at a desired site, some type of localization system must be used. To determine the relative position of the catheter to patient anatomy, magnetic localization systems have been developed that provide a location of the catheter within a well-known and controlled magnetic field and impedance localization systems have been developed that provide a location of the catheter within three pairs of electrodes using electrical currents. The externally-generated magnetic fields include precise magnetic gradients (field lines) that are sensed by the catheter (e.g., by elements such as coils) being located within the magnetic field. The currents induced by the magnetic field(s) in the sensors are analyzed using algorithmic processes and used to determine the position of the catheter within the patient's body. Once the catheter is positioned within the patient, as desired, a clinician can operate the catheter, for example, to ablate tissue to interrupt potentially pathogenic heart rhythms.

However, magnetic localization systems are susceptible to error induced by magnetic distortions within the magnetic field caused by, for example, extraneous ferrous or metallic objects intruding into the magnetic field. The introduction of such distortions can result in the system presenting an inaccurate position of the catheter within the patient's body.

BRIEF SUMMARY

It is desirable to provide a system for determining the position of a medical device within a body. In particular, it is desirable to provide a system that will reduce errors in position.

In one embodiment a system for differentiating between magnetic field distortion and physical movement in a hybrid magnetic and impedance tracking system for navigating a medical device within a patient can comprise an impedance localization system comprising a first drive patch and a second drive patch configured to be coupled to an external surface of the patient's body, the first and second drive patches configured to generate an electrical field within the body for locating an electrode on the medical device, a magnetic localization system configured to generate a magnetic field, a magnetic sensor coupled to one of the first and second drive patches and configured to receive signals from the magnetic localization system, and an electronic control unit configured to receive drive patch location data from the impedance localization system and magnetic sensor location data from the magnetic localization system. The electronic control circuit can be configured to detect a location change of the magnetic sensor and use the drive patch location data and magnetic sensor location data to determine whether the detected location change of the magnetic sensor is caused by a magnetic field distortion or a physical movement of the magnetic sensor.

In another embodiment a system for differentiating between magnetic field distortion and physical movement in a hybrid magnetic and impedance tracking system for navigating a medical device within a patient can comprise a magnetic localization system configured to generate a magnetic field, a magnetic sensor comprising a first sensor coil, a second sensor coil oriented orthogonal to the first sensor coil, and a third sensor coil oriented orthogonal to the first and second sensor coils and configured to receive signals from the magnetic localization system, a plurality of impedance patches configured to generate an electric field within the patient's body for locating an electrode on a medical device, and an electronic control unit configured to receive information from the magnetic sensor and the plurality of impedance patches. The electronic control unit can be configured to determine a magnetic sensor vector and an impedance vector, the electronic control circuit can be configured to detect a location change of the magnetic sensor and use the magnetic sensor vector and the impedance vector to determine whether the detected location change is caused by a magnetic field distortion or a physical movement of the magnetic sensor, and the electronic control unit can be configured to initiate a correction algorithm, wherein the correction algorithm is configured to correct a change in a position of the medical device based on the magnetic field distortion or by the physical movement of the magnetic sensor.

In yet another embodiment a method for differentiating between magnetic field distortion and physical movement in a hybrid magnetic and impedance tracking system for navigating a medical device within a patient can comprise receiving a first set of one or more signals from a magnetic sensor indicative of a magnetic field sensed by each of a plurality of sensor coils within the magnetic sensor at a first time, receiving a first set of one or more signals from an impedance sensor indicative of a position within a coordinate system, receiving a second set of one or more signals from the magnetic sensor indicative of the magnetic field sensed by each of the sensor coils at a second time, receiving a second set of one or more signals from the impedance sensor indicative of a position within the coordinate system, determining a magnetic sensor vector, determining an impedance vector, detecting a location change of the magnetic sensor, comparing the magnetic sensor vector to a first threshold and the impedance vector to a second threshold to determine whether the detected location change of the magnetic sensor is caused by a magnetic field distortion or a physical movement of the magnetic sensor has occurred. The detected location change can be caused by a magnetic field distortion if the magnetic sensor vector is over the first threshold and the impedance vector is under the second threshold, and the detected location change can be caused by a physical movement of the magnetic sensor if the magnetic sensor vector is over the first threshold and the impedance vector is over the second threshold.

The foregoing and other aspects, features, details, utilities and advantages of the present invention will be apparent from reading the following description and claims, and from reviewing the accompanying drawings. Additional features, advantages, and embodiments of the disclosure can be set forth or apparent from consideration of the detailed description and drawings. Moreover, it is to be understood that the foregoing brief summary and the following detailed description, drawings, and attachment are intended to provide further explanation without limiting the scope of the disclosure as claimed.

DETAILED DESCRIPTION

Figure 1:
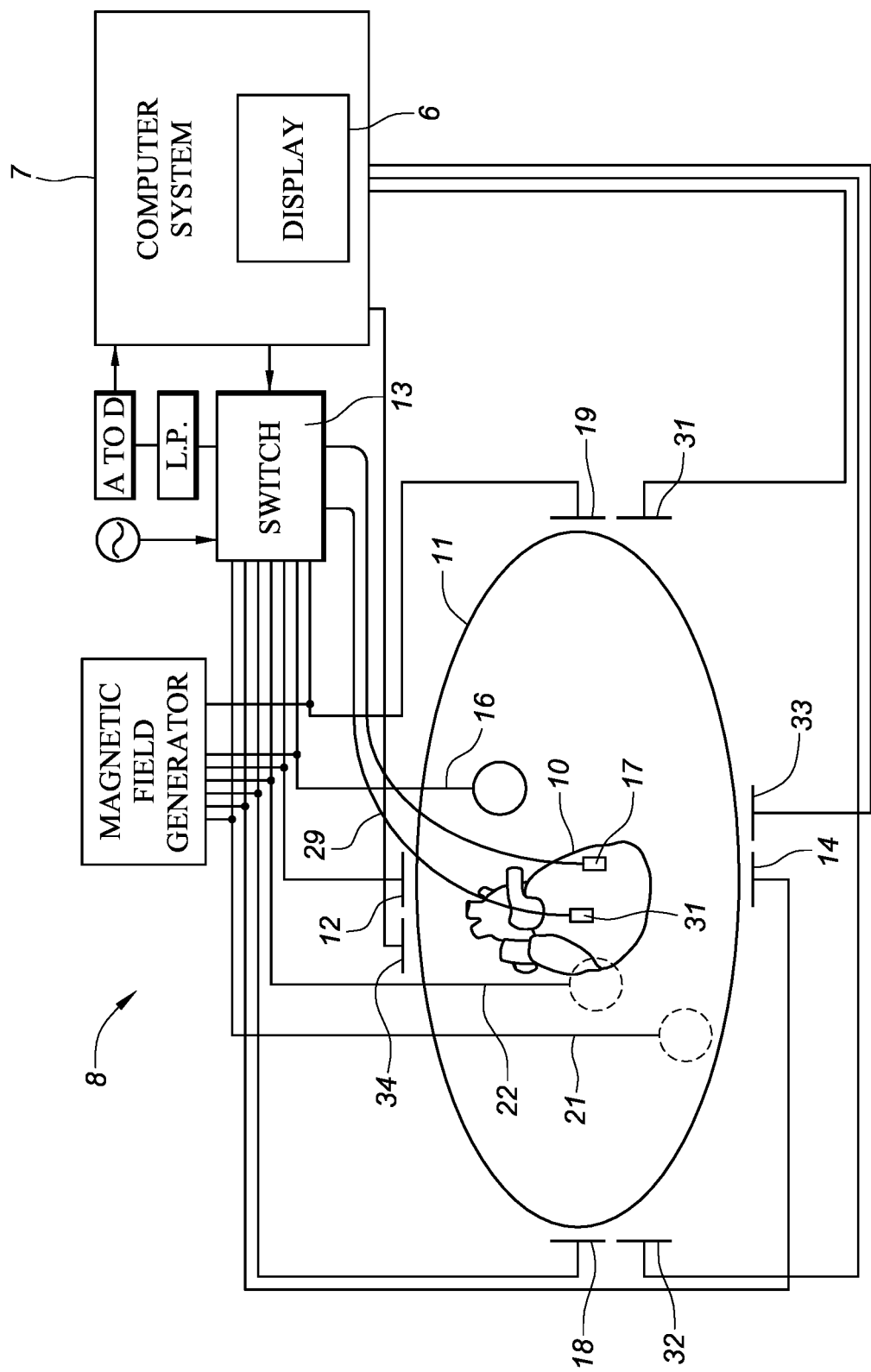
FIG. 1 is a schematic diagram of a hybrid magnetic and impedance tracking system, consistent with various aspects of the present disclosure.

Cardiac localization systems are capable of displaying a three-dimensional (3D) position of conventional electrophysiology catheters within an overlaid model or image of a cardiac chamber. These localization systems can also display cardiac electrical activity as waveform traces and as dynamic 3-D isopotential maps on the model of the cardiac chamber. The contoured surfaces of these three-dimensional models are based on the anatomy of the patient's own cardiac chamber. These localization systems can use impedance based and/or magnetic based localization technologies to render catheter position and model creation.

When using magnetic localization, the magnetic fields generated from a local source are inherently susceptible to distortions caused by metallic or ferrous objects intruding into, or being placed adjacent to, the generated magnetic fields. Such distortions can cause inaccuracies in calculated or determined medical device locations and in related anatomical models and other representations. Additionally, when using magnetic localization systems and impedance localization systems, patient movement can cause distortions and inaccuracies in the calculated or determined medical device locations and in related anatomical models and other representations. Navigation systems can employ various sensors to monitor movement of the patient in order to compensate for this movement in determining the position of the medical device. Additionally, as discussed herein, the navigation system can pair magnetic and impedance sensors to determine whether magnetic distortions or patient movement have occurred.

Magnetic sensors embedded within intracardiac devices are used to determine position and orientation of the device with respect to one or more known reference positions. These devices can comprise catheters, sheaths, guidewires, and other devices known to one of ordinary skill in the art. Additionally, impedance sensors embedded within intracardiac devices can be used to determine a position and orientation of such devices. This position and orientation information can be used to navigate the device and can also be used to optimize magnetic and impedance-based device localization. When navigating medical devices in space, the displayed or otherwise reported positions of the devices can notably shift (e.g., visually shift on a screen displaying a representation of the location of the device) when the underlying magnetic field is changed/distorted or the position of the patient has changed despite no actual change (or minimal actual change) in the device's physical location within the patient. Understandably, this shift can cause inaccuracies to models created using the reported locations of the devices. Magnetic position and orientation data from devices can also be used in conjunction with impedance-based localization technologies and used to optimize/scale non-linear impedance fields. Embodiments of the present disclosure, as described in more detail below with reference to the figures, identify the existence of such distortions within a magnetic field and changes in readings as a result of patient movement, the presence of other devices inserted into the patient as well as disturbances within the surrounding environment. Embodiments of the present disclosure can further differentiate between such distortions within a magnetic field and changes in readings as a result of patient movement after determining a distortion or movement is present.

FIG. 1 shows a schematic diagram of a hybrid magnetic and impedance tracking system 8 used for navigating the human anatomy of a patient 11 (depicted, for simplicity's sake, as an oval in FIG. 1) while conducting a medical procedure. For example, as shown in FIG. 1, the system 8 can be used to map a heart 10 of the patient and to navigate a cardiac catheter through the chambers of the heart. Hybrid magnetic and impedance tracking system 8 determines the location (and, in some embodiments, the orientation) of objects (e.g., a portion of a diagnostic or ablation catheter, such as the electrode assembly 112 depicted in FIGS. 2A and 2B), typically within a three-dimensional space, and expresses those locations as position information determined relative to at least one reference. Specifically, the hybrid magnetic and impedance tracking system 8 can be used to determine the location of the cardiac catheter within a magnetic and/or impedance field, which is then overlaid onto, for example, an image or a model of the heart 10. In other embodiments, magnetic resonance imaging data, among other reference data can be overlaid onto the three-dimensional space to provide a clinician with a virtual work environment in which to reference for real-time position of the cardiac catheter relative to the patient's heart 10.

The hybrid magnetic and impedance tracking system 8 can include various visualization, localization, mapping, and navigation components. For example, hybrid magnetic and impedance tracking system 8 can partly comprise a magnetic-field-based system such as the CARTO™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another embodiment, the hybrid magnetic and impedance tracking system 8 can partly comprise a magnetic field based system such as the MEDIGUIDE™ Technology system available from Abbott Laboratories., and as generally shown with reference to one or more of U.S. Pat. Nos. 6,233,476; 7,197,354; 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/IB2014/059709 entitled "Medical Device Navigation System" filed on 13 Mar. 2014, the disclosures of which are hereby incorporated by reference in their entireties as though fully set forth herein. In yet another embodiment, hybrid magnetic and impedance tracking system 8 can comprise a hybrid electric-field-based and magnetic-field-based system, such as, for example and without limitation, the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set fully forth herein, or the CARTO™ 3 system commercially available from Biosense Webster. In some embodiments, the hybrid magnetic and impedance tracking system 8 can comprise or be used in conjunction with other commonly available systems, such as, for example and without limitation, fluoroscopic, computed tomography (CT), and magnetic resonance imaging (MRI)-based systems. For purposes of clarity and illustration only, the localization system 8 will be described hereinafter as comprising a hybrid magnetic and impedance tracking system.

The hybrid magnetic and impedance tracking system 8 can include various visualization, localization, mapping, and navigation components. For example, hybrid magnetic and impedance tracking system 8 can partly comprise an impedance localization system and/or hybrid magnetic and impedance tracking system such an EnSite™ NavX™ Electro Anatomical Mapping System, an EnSite™ Velocity™ Electro Anatomical Mapping System, and an EnSite Precision™ Electro Anatomical Mapping System, all commercially available from Abbott Laboratories, or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application), or US Publication No. 2018/0296111 A1, U.S. application Ser. No. 15/953,155 filed 13 Apr. 2018 (the '155 application). The '397 patent, the '580 application, and the '155 application are all hereby incorporated by reference as though fully set forth herein. The various EnSite™ systems are based on the principal that when electrical currents are passed through the thorax a voltage drop occurs across internal organs such as the heart and this voltage drop can be measured and used to determine the position of a medical device within the body.

FIG. 1 can further exemplify a hybrid localization system including two localization systems: an impedance-based localization system and a magnetic-based localization system. In general, and as shown in FIG. 1, hybrid magnetic and impedance tracking system 8 can include a plurality of magnetic field transmitters (e.g., 12, 14, 16, 18, 19, and 21) that emit a magnetic field across the patient's body 11. These magnetic field transmitters, which can be placed upon or attached/applied to the patient, or fixed to an external apparatus, define three generally orthogonal axes, e.g., an x-axis, a y-axis, and a z-axis. The magnetic field transmitters are electrically coupled to a magnetic field generator. The magnetic field generator generates one or more magnetic fields that can be transmitted simultaneously, time multiplexed, and/or frequency multiplexed via the magnetic field transmitters. A switch 13 samples the signals received from one or more of receivers 17, 22, and 31 (e.g., a catheter, a patient reference sensor, an internal reference sensor, a magnetic sensor, etc.).

The system can additionally include three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. FIG. 1 illustrates two pairs of these orthogonally located drive patches 31, 32, 33, 34. Sinusoidal currents can be driven through each pair of patch electrodes to create an electric field and voltage measurements for one or more electrodes associated with the medical device can be obtained. The measured voltages are proportional to the distance of the device electrodes from the patch electrodes. The measured voltages are compared to the potential at the reference electrode and a position of the device electrodes within the coordinate system of the navigation system is determined.

The received signals from the receivers, indicative of the magnetic field that traversed through the patient's body 11 from one or more of the transmitters, and/or the impedance data from the plurality of drive patches are then converted from an analog to a digital signal for further processing by the computer system 7. The computer system 7 performs computations on the data received from the receivers and/or drive patches to determine, for example, the location of a cardiac catheter within the patient's heart. In the illustrated embodiment, the computer system can be coupled to both the magnetic tracking system and the impedance tracking system. In other embodiments, the magnetic tracking system and the impedance tracking system can be coupled to separate devices or additional components can be present within the system. Additionally, the actual catheter position can be obscured by magnetic distortions within the magnetic field caused by other ferrous/metallic bodies. These magnetic distortions are associated with an error rate of the perceived position of the catheter compared to the actual position of the catheter. The computer can additionally comprise an electronic control unit. As described throughout the application, the computer can receive, compute, determine, and send data from the various apparatus and systems described herein.

For reference by a clinician during a procedure, the perceived location of the catheter within the magnetic field can be presented on a display 6 in relation to known reference points, e.g., cardiac chambers, arteries, etc.

In one embodiment, a medical device such as a catheter, can extend into the left ventricle of the patient's heart 10. In other embodiments, a medical device can extend into the left atrium, the coronary sinus, the pulmonary veins, or another artery, vein, or lumen within the body. In some of these embodiments, the medical device can be used outside of the vascular system. The catheter includes a plurality of sensor coils and electrodes spaced along its length. As used herein, the term "sensor coils" generically refer to any element whose position within a magnetic field can be measured by that system (e.g., magnetic sensors). Because each sensor coil lies within the magnetic field, localization data can be collected simultaneously for each sensor coil. Additionally, each of the electrodes is located within field created by the impedance drive patches, localization data can also be collected simultaneously for each electrode.

A hybrid magnetic and impedance tracking system 8 can include a fixed reference 22 to define the origin of the magnetic-based localization system's coordinate frame. This fixed reference provides a relative position to which the positions of sensor coils on the catheter are measured. Such a fixed reference can likewise be in a fixed internal or external location. Likewise, multiple references can be used for the same or different purposes (e.g., to correct for respiration, patient shift, system drift, or the like). If the fixed reference comprises a magnetic reference sensor, the magnetic reference sensor can be susceptible to metallic interference as well as physical movement of the magnetic reference sensor, whether through movement of the patient, skin movement or stretching, accidental movement, or other method. Further, as the fixed reference 22 is used to define the origin of the magnetic-based localization system's coordinate frame, a physical movement of the fixed reference would not be observed in the tracked tools positional data. The combination of magnetic field distortions and physical movement of the fixed reference 22 can require a system that can differentiate between the types of error. The present system can discern between physical patient movements and perceived movement which was caused by magnetic field distortion by using a combination of both location data from an impedance based navigation system in conjunction with magnetic location data from a magnetic based navigation system. A magnetic reference sensor can be physically connected to a patient applied patch or other means which allows for tracking using the hybrid magnetic and impedance tracking system, i.e. EnSite Precision™. As the location of the patch and magnetic reference sensor are now tied together, the relative location of the patch to the magnetic reference sensor can be monitored. As described herein, if both impedance location data of the patch or other impedance device and the magnetic reference sensor location data move together, then this can be attributed to patient (physical) movement. However, if the magnetic location data of the reference changes, but the impedance location data does not, then it can be determined the magnetic reference sensor is being disturbed by interference.

A computer system, which can comprise a conventional general-purpose computer, a special-purpose computer, a distributed computer, or any other type of computer, and which can comprise one or more processors, such as a single central processing unit (CPU), or a plurality of processing units, commonly referred to as a parallel processing environment, can control hybrid magnetic and impedance tracking system 8 and/or execute instructions to practice the various aspects of the embodiments described herein.

Figures 2A, 2B:
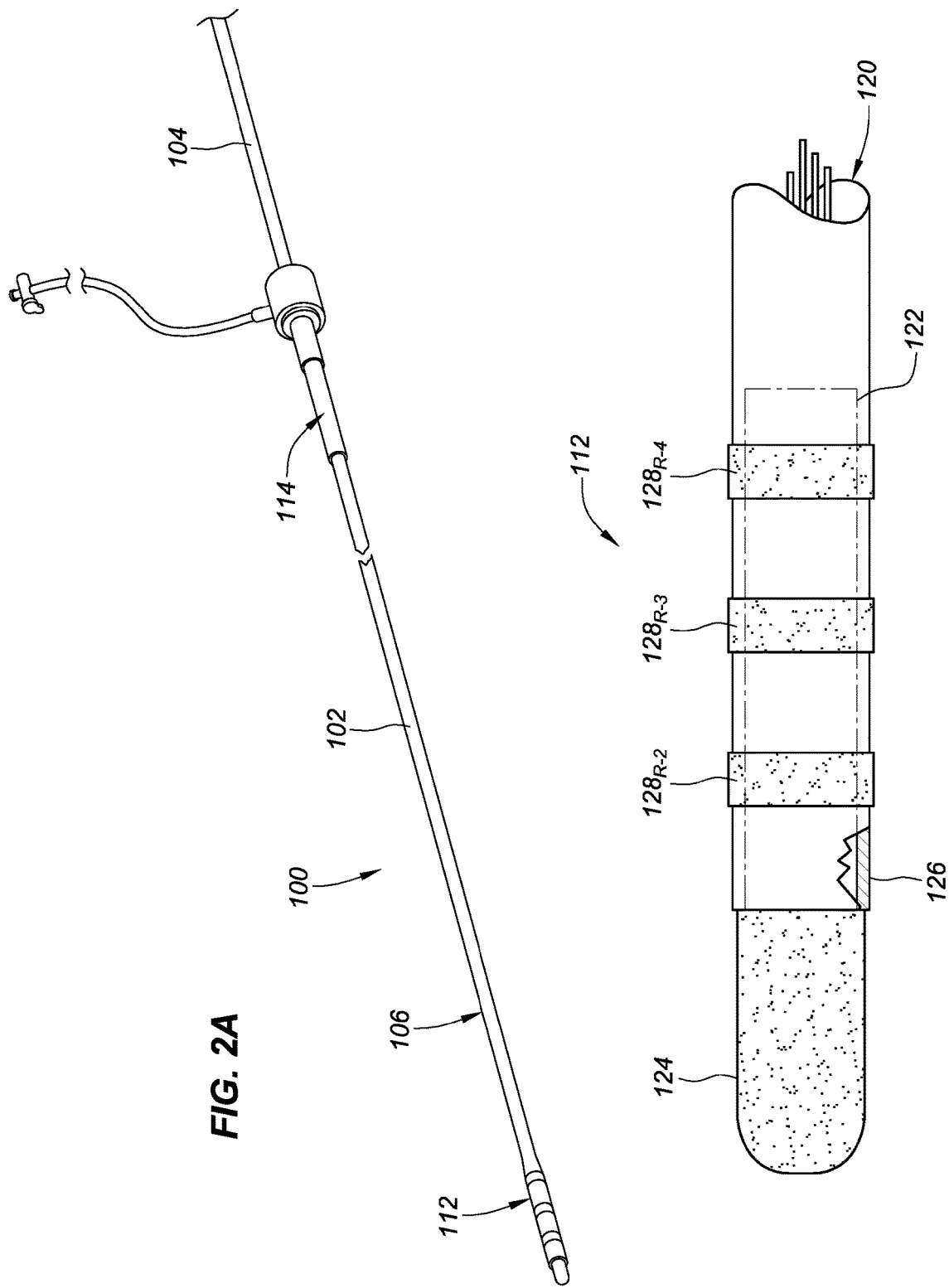
FIG. 2A is a fragmentary, isometric view of a catheter assembly comprising a catheter configured for localization in a hybrid magnetic and impedance tracking system and an introducer, consistent with various aspects of the present disclosure.
FIG. 2B is an enlarged, fragmentary side view of the distal tip assembly of the catheter of FIG. 2A, consistent with various aspects of the present disclosure.

FIG. 2A is a simplified, isometric view of a catheter assembly 100, comprising a catheter 106 that includes a catheter tip assembly (or an electrode assembly or distal tip assembly) 112 at a distal end portion and operatively adapted for conducting a diagnostic or a therapeutic procedure under clinician control. A proximal end portion 104 of the catheter 106 can include a steering handle or other mechanism (not shown). In the present embodiment, catheter 106 is a mapping catheter. The catheter 106 includes a flexible shaft 102 extending between the proximal end portion 104 and the catheter tip assembly 112. The catheter assembly 100 further includes an electrical connector (not shown) configured to establish electrical connection(s) between the catheter tip assembly 112 and external electrical components (not shown) to perform, for example, localization, mapping, ablation, and/or pacing procedures. FIG. 2 further shows an introducer 114 comprising part of the catheter assembly 100. The catheter tip assembly 112 can comprise a plurality of sensors coils (or localization coils or sensors) such as those shown schematically in, for example, FIGS. 3A, 3B, and 3C of the present application, or the sensors shown in U.S. Pat. No. 6,690,963 (see, e.g., sensors 30, 32, 34 depicted in FIGS. 2 and 3), which has been incorporated herein by reference as though fully set forth herein. These localization coils can be located, for example, in the region shown by the dashed box 122 in FIG. 2B.

FIG. 2B is an enlarged, side view showing, in greater detail, the tip assembly 112. The tip assembly 112 includes a tip electrode 124 (schematically shown in FIG. 2B); a plurality of ring electrodes 128R-2, 128R-3, and 128R-4; and a plurality of electrical conductors 120 (e.g., one conductor electrically connected to each of the three ring electrodes and a separate conductor electrically connected to the tip electrode 124). Additional electrical connectors can extend proximally from the tip assembly 112 if localization coils are located in, for example, the area outlined by dashed box 122.

Figure 3A:
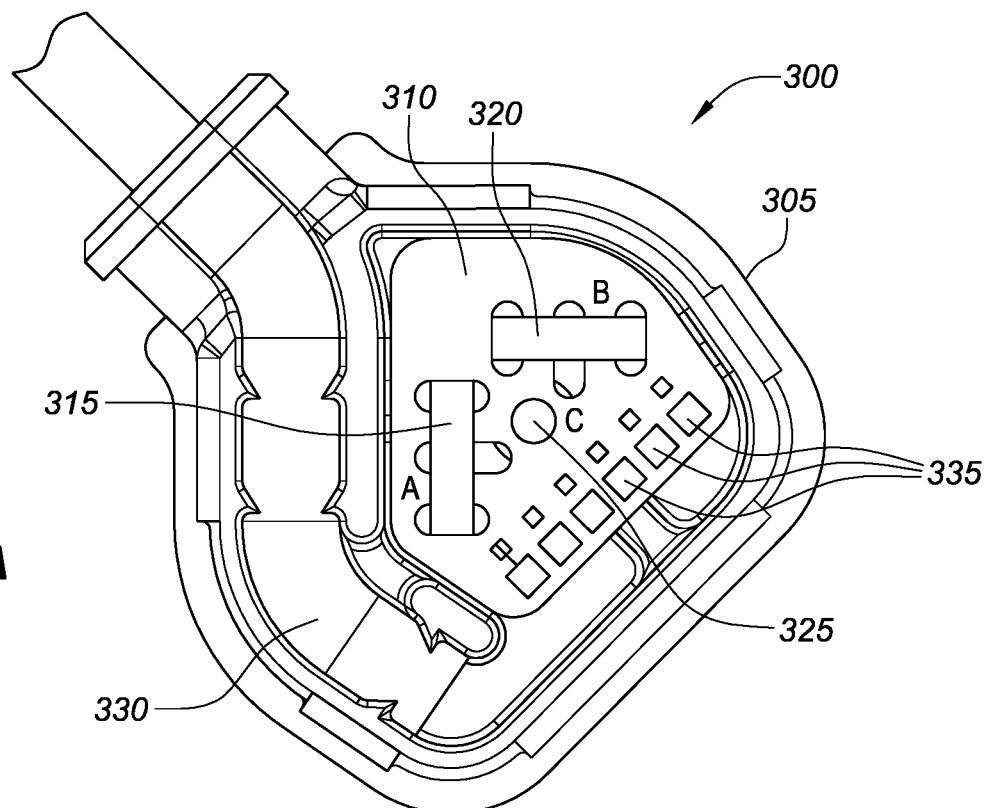
FIG. 3A is a top view of a magnetic detection sensor, consistent with various aspects of the present disclosure, with portions of the sensor housing broken away to reveal internal features.
Figure 3B:
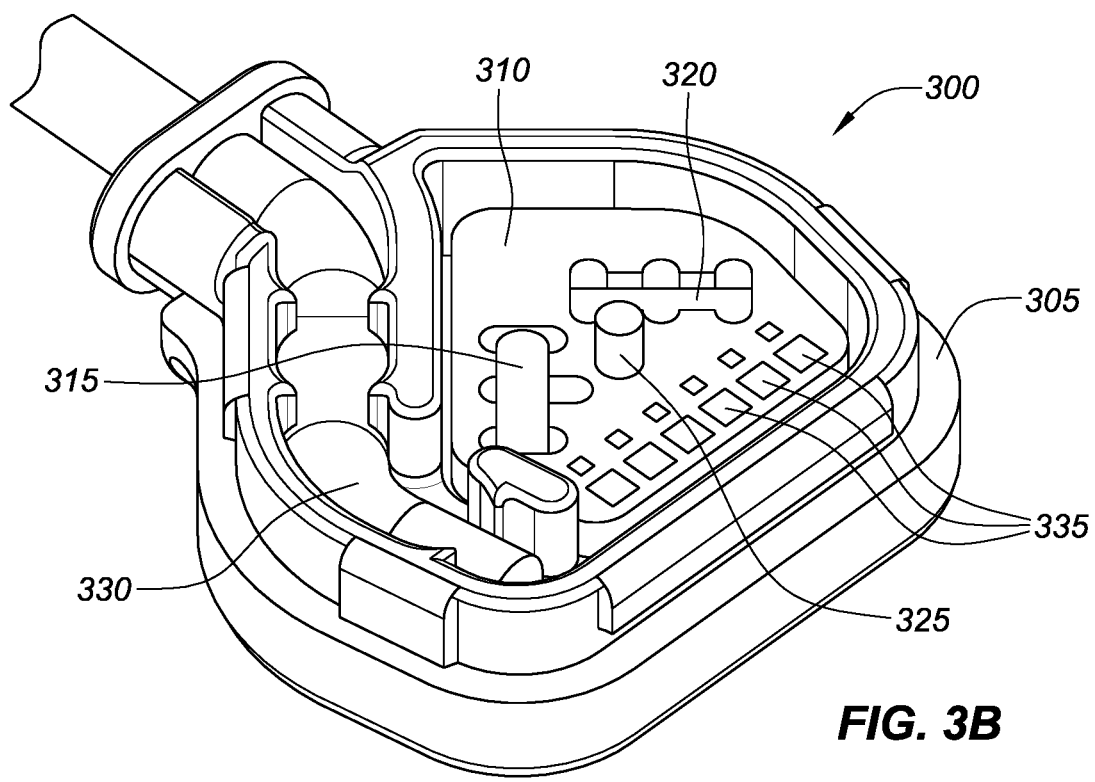
FIG. 3B is an isometric view of the magnetic detection sensor of FIG. 3A, consistent with various aspects of the present disclosure.

FIGS. 3A and 3B are views of one embodiment of a magnetic sensor 300 including a circuit board 310 that is electrically coupled to first, second, and third sensor coils 315, 320, and 325, respectively. In some embodiments, the magnetic sensor can comprise the fixed reference to define the origin of the magnetic-based localization system's coordinate frame. In other embodiments, the magnetic sensor can comprise more or less sensor coils than used in FIGS. 3A and 3B. In one embodiment, a magnetic sensor can comprise 5 sensor coils. In another embodiment, a magnetic sensor can comprise 6 sensor coils. Each of the sensor coils are affixed relative to the magnetic sensor housing 305 and the circuit board 310, with the sensor coils fixed, in the illustrated embodiment, in orthogonal orientations relative to one another. In additional embodiments, the sensor coils can be fixed in varying orientations. In some embodiments, the sensor coils can comprise parallel, offset, or additional orientations. During operation, the magnetic sensor 300 is placed within a generated magnetic field and each of the respective sensor coils receive energy indicative of the strength and orientation of the magnetic field. In one specific embodiment, a vector sum of the received energy is computed to determine a perceived change in the position of the sensor coils relative to one another. A perceived change being indicative of a magnetic distortion in the magnetic field proximal the magnetic sensor. In medical magnetic localization applications (as discussed in more detail above), such magnetic distortions affect the ability of the system to accurately locate a position of, for example, a catheter within the patient's body.

Before transmitting the received signals from the first, second, and third sensor coils 315, 320, and 325, respectively, to computing circuitry for processing and for determination of the amount of distortion in the magnetic field, circuitry within circuit board 310 can conduct a number of signal processing functions including, e.g., analog-to-digital conversion, pre-amplification, and signal noise filtration. After signal processing, the received signals are transmitted to magnetic localization system processor circuitry via cable 330 which is coupled to the circuit board 310 via bonding pads 335. In further embodiments, the magnetic sensor can wirelessly transmit the received signals from each of the sensor coils to the processor circuitry of the magnetic localization system using wireless data transmission protocols known to one of skill in the art.

Figure 3C:
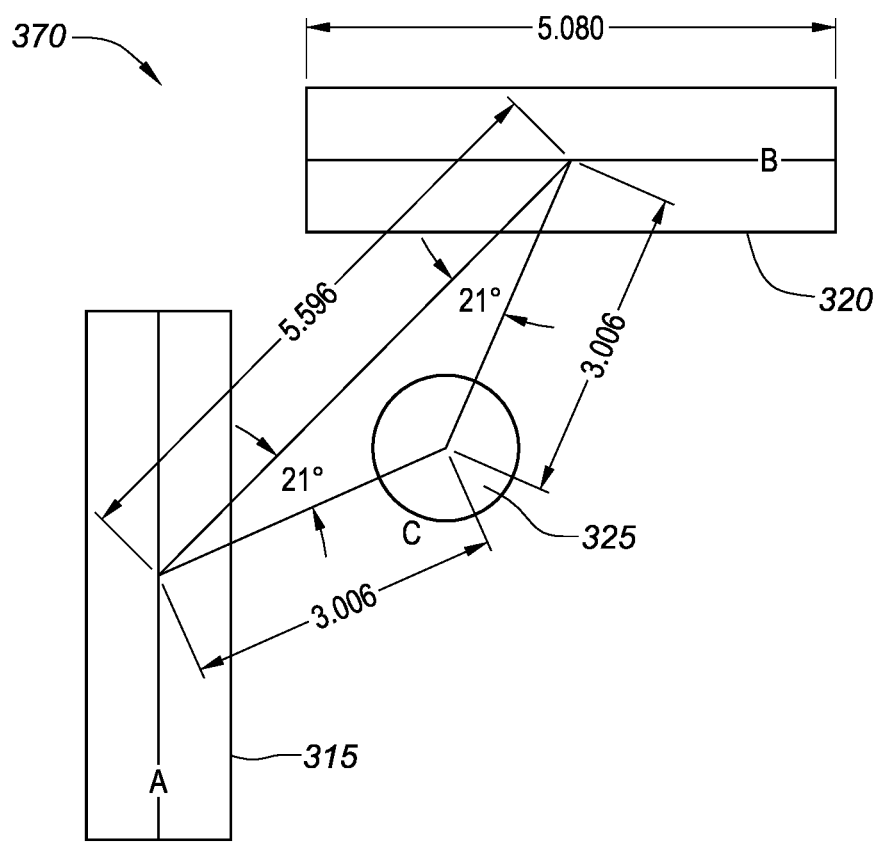
FIG. 3C is an enlarged top view of an embodiment of a sensor coil array configuration broken away from, for example, the magnetic detection sensor of FIGS. 3A and 3B, consistent with various aspects of the present disclosure.

FIG. 3C shows an embodiment of a sensor coil array 370 (including first, second, and third sensor coils, 315, 320, and 325, respectively), exploded away from the housing 305, circuit board 310, and other components shown in FIGS. 3A and 3B. As shown in FIG. 3C, the sensor coils are oriented orthogonal to one another and affixed at precise distances from each other. As stated above, while the illustrated embodiments of the sensor coils are oriented orthogonal to one another, additional orientations are possible. During operation of the magnetic sensor in a magnetic field, the output of the sensor coil array is used to calculate magnitude positions and orientations associated with the mechanical position and orientation of the sensor coils relative to one another.

Figure 3D:
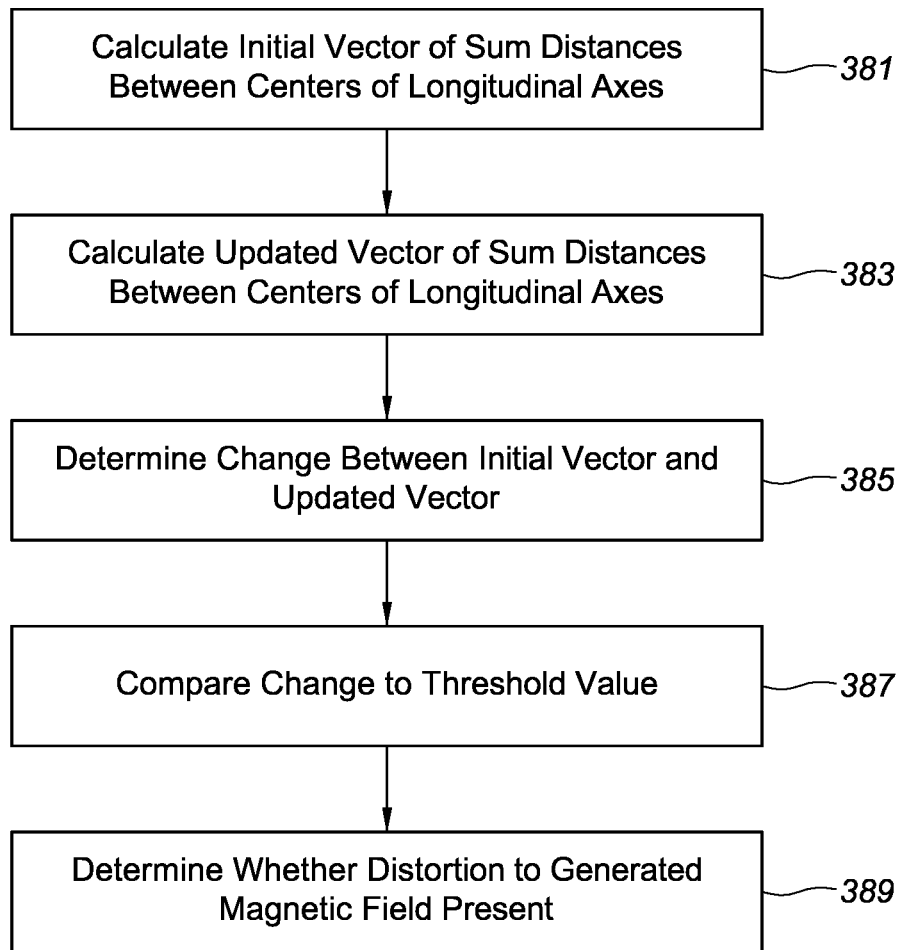
FIG. 3D illustrates a flowchart detailing a method of calculating magnitude positions and orientations associated with the mechanical position and orientation of the sensor coils relative to one another.

FIG. 3D illustrates one method of calculating magnitude positions and orientations associated with the mechanical position and orientation of the sensor coils relative to one another.

In Step 381 the vector sum of the distances are calculated between the centers of the longitudinal axes of the three sensor coils at a first time. The vector sum can also be considered an initial index value. In response to a distortion in the magnetic field, the perceived location of one (or more) of those sensor coils can be displaced from its known/fixed location relative to the other sensor coils. As a result, the corresponding vector sum would be correspondingly affected.

In Step 383 an updated vector sum of the distances are calculated between the centers of the longitudinal axes of the three sensor coils at a second time. The updated vector sum can also be considered a current index value.

In Step 385, a change between the initial vector sum and the updated vector sum can be determined.

In Step 387, the change between the initial vector sum and the updated vector sum can be compared to a determined threshold. The determined threshold can be indicative of a distortion to the generated magnetic field. This distortion can make readings from the generated magnetic field unreliable.

In Step 389, a determination is made whether a distortion to the generated magnetic field is present.

In additional embodiments, after determining the initial index-value (where the magnetic field is free of distortions), subsequent magnitude positions and orientations can be correlated timewise. As stated above, these later magnitude values can vary from the initial index-value due to localized magnetic distortions within the magnetic field, resulting in a perceived skewing of the location and orientation of the sensor coils relative to one another (even though the orientation and position of the sensor coils to one another are fixed). The initial index-value can be compared to subsequent index-values to determine when acceptable levels of magnetic field distortion during a medical procedure are exceeded. This delta value (the change in value between the initial index-value and a subsequent index-value) is associated with distortion related drift in the localization of the catheter.

In one embodiment, an acceptable delta value for magnetic distortion can be determined by the clinician (e.g., a soft threshold value), and/or the processor circuitry (e.g., a hard threshold value). In another embodiment, an acceptable delta value for magnetic distortion can be preset within the system. In yet other embodiments, the system can suggest one or more acceptable delta values for magnetic distortion based on various factors for the clinician to select. In one such embodiment, the magnetic localization system can indicate that a distortion is affecting the perceived location of the catheter within the patient upon exceeding the soft threshold value, but continue displaying the perceived location of the catheter on the display. In another embodiment, when the delta value of the index-value exceeds a hard threshold value, the magnetic localization system can no longer update the display with the newly-calculated perceived location of the catheter due to the perceived inaccuracy of the location information. This information can be conveyed to the clinician through the use of audible, visual, haptic, or other sensory feedback. In some embodiments, this operation can be called magnetic mode. Magnetic mode can comprise stopping the display of a location of the medical device or provide a visual indicator showing the location is no longer accurate. In some embodiments, the visual indicator can comprise a ghost image or flashing electrodes to illustrate that the location is no longer accurate. In other embodiments, the hybrid magnetic and impedance tracking system can revert or limit the location sensing to impedance location data only when the system detects that the delta value exceeds the hard threshold value and the magnetic localization system is unable to update the display. In one embodiment, the hybrid magnetic and impedance tracking system can automatically change location sensing of a medical device to only rely on the impedance location sensing when the system determines a magnetic distortion is affecting the system. In other embodiments, the hybrid magnetic and impedance tracking system can signal to the user that a magnetic distortion is present and the user can then select the option to proceed by only sensing impedance location data of a medical device. In some embodiments, this operation can be called impedance mode. In various embodiments, the impedance location sensing mode can continue until the magnetic distortion is no longer affecting the system, at which point, the system can automatically switch back to using the magnetic tracking system the same as before the magnetic distortion was present. In other embodiments, the impedance location sensing mode can continue until the magnetic distortion is no longer affecting the system, at which point, the system can signal to a user whether they want to switch back to using the magnetic tracking system the same as before the magnetic distortion was present. In other embodiments where a switch to impedance only mode does not occur, once the calculated index-value falls back below the hard threshold value, the magnetic localization system can resume updating the display with the perceived location of the catheter within the patient. In other embodiments, when the delta value of the index-value exceeds a hard threshold value the system can continue displaying the perceived location of the catheter on the display. In various embodiments, the system can display this to the clinician as described herein.

As shown in FIG. 3C, a specific experimental/detailed configuration of the sensor coil array 370 is presented. First sensor coil 315 is orientated orthogonal to both second sensor coil 320 and third sensor coil 325. Accordingly, each of the sensor coils is oriented planar to one of three dimensional axes, and receives magnetic field energy that is substantially co-axial with the sensor coil. In the illustrated embodiment, a center-point of the first coil can be spaced 5.596 millimeters (mm) from a center point of the second sensor coil, and the center-point distance between the first and second sensor coils and the third and second sensor coils can be 3.006 mm, with an angular offset of the second and third sensor coils relative to the first sensor coil being 22 degrees, and an angular offset of the first and third sensor coils relative to the second sensor coil also being 22 degrees. In other embodiments other relative positions and orientations of the sensor coil array can also be utilized.

During operation of the magnetic localization system utilizing a sensor coil array 370 (as shown in FIG. 3C), the calculated magnitude values of the sensed magnetic field rely on the fixed spacing of the sensor coils to determine when magnetic distortion in the magnetic field is resulting in catheter location data that is excessively skewed.

While the magnetic sensors as described herein could be used by themselves to detect magnetic field distortion, there can be instances where a distortion can cause all of the coils within a magnetic sensor to move in the same direction. As a result, the distortion would not be correctly detected. To mitigate these instances, at least one magnetic sensor can be place on at least one impedance patch.

Figure 4:
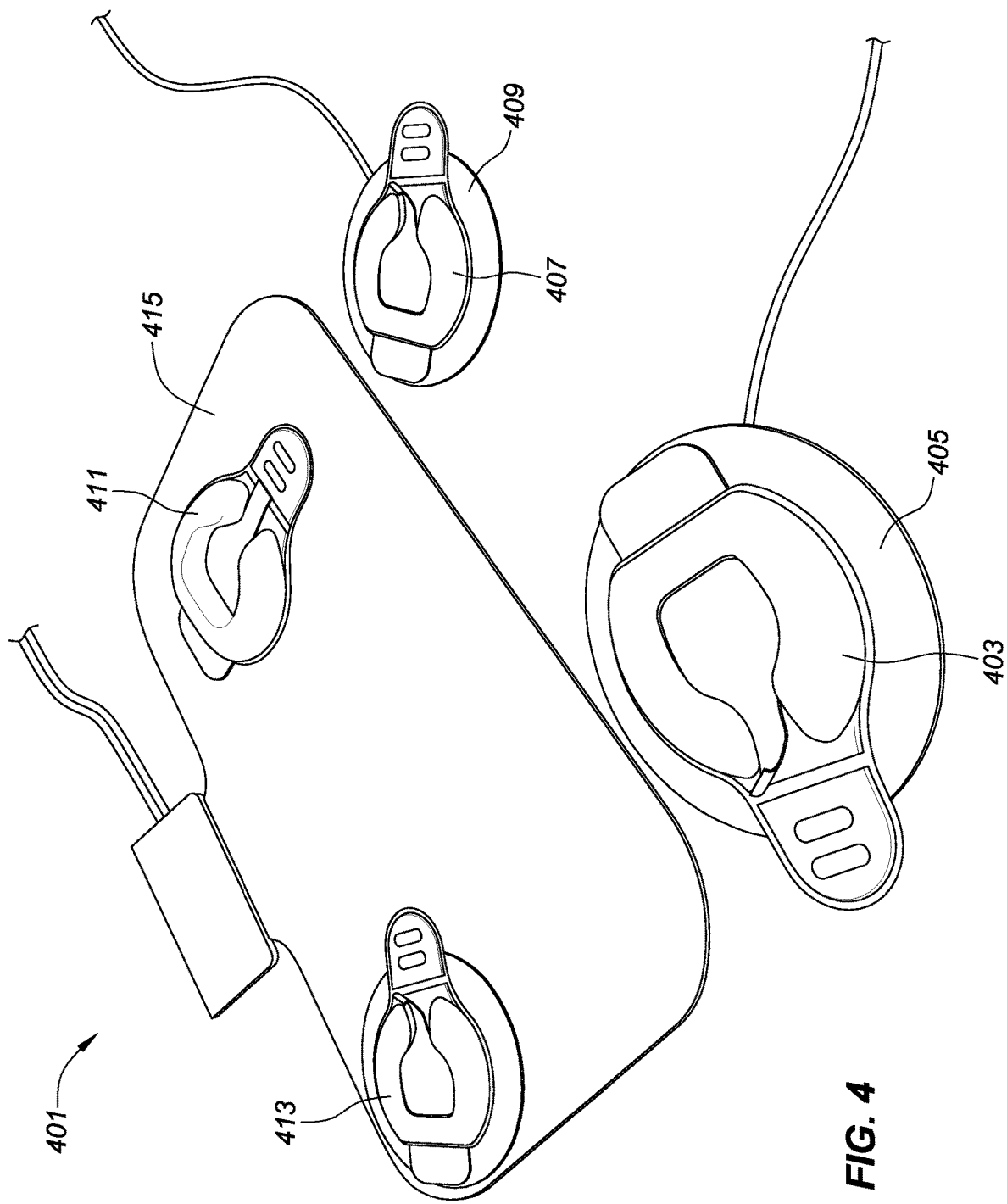
FIG. 4 is an isometric view of placement of magnetic sensors on impedance patches in a hybrid magnetic and impedance tracking system.

FIG. 4 illustrates an isometric view of a plurality of magnetic sensors disposed on a plurality of impedance patches in a hybrid magnetic and impedance tracking system 401. In the illustrated embodiment, a first magnetic sensor 403 can be placed on a first impedance patch 405, a second magnetic sensor 407 can be placed on a second impedance patch 409 and a third magnetic sensor 411 and a fourth magnetic sensor 413 can be placed on a third impedance patch 415. In the illustrated embodiment, the third impedance patch 415 can comprise a reference patch. Additionally, as illustrated, the third impedance patch 415 can comprise two magnetic sensors coupled thereto. In various embodiments, the magnetic sensors can be disposed on different patches within the orthogonal patch system. In one embodiment, a first magnetic sensor can be disposed on a neck patch, a second magnetic sensor can be disposed on a right side patch, and the third and fourth magnetic sensors can be disposed on the reference electrode. In another embodiment a first magnetic sensor can be disposed on a chest patch, a second magnetic sensor can be disposed on a back patch, a third magnetic sensor can be disposed on a right patch, and a fourth magnetic sensor can be disposed on a reference electrode. In other embodiments additional arrangements and numbers of magnetic sensors can be placed on the impedance sensors. The impedance patches can be placed on a patient as described throughout the application.

Figure 5:
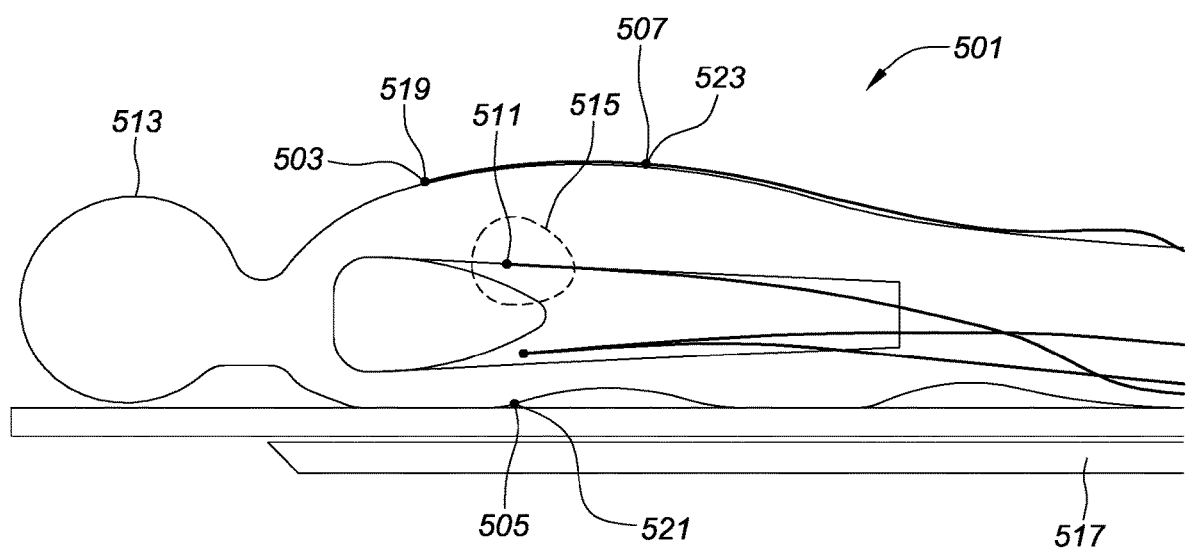
FIG. 5 is an side view of a placement of magnetic detection sensors on a patient during a medical procedure, consistent with various aspects of the present disclosure.

FIG. 5 shows an embodiment of a hybrid distortion detection system 501. The illustrated system depicts a placement of magnetic sensors on impedance patches relative to a patient 513 during a medical procedure where magnetic localization of a medical device within a patient is utilized. The illustrated embodiment depicts one possible placement of a front impedance patch 503, a back impedance patch 505, and a reference impedance patch 507. The illustrated embodiment further includes a first magnetic sensor 519 coupled to the front impedance patch 503, a second magnetic sensor 521 coupled to the back impedance patch 505, and a third magnetic sensor 523 coupled to the reference impedance patch 507. In the present embodiment, the front impedance patch 503 is placed anterior to the patient 513 (e.g., on a patient's chest), while the back impedance patch 505 is placed posterior to the patient (e.g., between a patient's back and an operating table 517). The impedance system can also include additional orthogonally oriented patches (not shown) as described herein. In one embodiment, the first and second magnetic sensors are ideally located adjacent (and opposite one another) to the anatomy of the patient where the procedure is being conducted. As shown in FIG. 5, the first and second magnetic sensors are opposite one another relative to the heart 515, which is receiving treatment by way of catheter 511, which is extended into the heart.

As described herein, magnetic field transmitters surrounding the patient emit a magnetic field used to determine the position of the catheter. Specifically, the catheter, including a coil in its tip region, senses the magnetic field in proximity to the coil. Processing circuitry can then determine, based on the sensed magnetic field at the tip of the catheter, where the coil is located in the magnetic field and, therefore, where the tip of the catheter is located. Additionally, the impedance patches can be used to determine the position of at least one electrode on the catheter. However, egress of other ferrous objects into the magnetic field create magnetic distortions within the field that affect localization of the catheter within the field. Additional movement of the patient can also affect localization of the catheter within the field. Accordingly, the first magnetic sensor 519 detects magnetic distortions in proximity to the anterior of the patient (e.g., medical instruments and equipment), and the second magnetic sensor 521 detects magnetic distortions in proximity to the posterior of the patient (e.g., ferrous objects associated with the operating room table, or other objects in the magnetic field there below). In such a configuration, magnetic distortions can be identified and a determination can be made as to the effect of the magnetic distortion on the catheter (e.g., whether the magnetic field in proximity to the catheter is being excessively affected by the magnetic distortion). As the at least one magnetic sensor is disposed on an impedance patch, additional information regarding magnetic field distortion and patient movement can also be determined.

During a medical procedure, a plurality of impedance patches and a plurality of sensor coils can be placed within a magnetic field. Each of the respective sensor coils, in each of the respective magnetic field distortion sensors can receive energy indicative of the strength and orientation of the magnetic field. The orthogonally located impedance patches can be coupled with at least one magnetic sensor comprising a plurality of sensor coils can be placed within a magnetic field produced by a hybrid localization system for the purposes of detecting a magnetic distortion or physical movement in proximity to a medical device within a patient. A hybrid localization system utilizes both impedance-based and magnetic field-based localization methodologies to more accurately determine the medical devices location. Each of the respective sensor coils, in each of the respective magnetic field distortion sensors, can receive energy indicative of the strength and orientation of the magnetic field. A perceived change over time, of the received energy while observing no change in the impedance position, is indicative of a magnetic distortion in the magnetic field proximal to the magnetic sensor. Alternatively, a perceived change over time, of the received energy while also observing a change in the impedance position, is indicative of a physical movement of the impedance patch and the magnetic sensor attached thereto.

One example of such a system is the EnSite Precision™ mapping system commercially available from Abbott Laboratories. The EnSite Precision™ mapping system can utilize both impedance-based and magnetic field-based localization methodologies (e.g., a hybrid system). Impedance measuring patches can be electrically coupled to the patient. In some implementations of the EnSite Precision™ mapping system, the impedance measuring patches can be placed on a patient's chest, on either side of a patient's chest, and on at least one of a patient's legs. Based on the varying impedance values detected by the impedance measuring patches an impedance-based location of the medical device can be determined.

In one embodiment, a vector sum of the received energy is computed to determine a perceived change in the position of the sensor coils relative to one another (and/or the perceived change in the position of the magnetic field distortions sensors relative to one another). A perceived change being indicative of a magnetic distortion in the magnetic field adjacent to the impedance patches and sensor coils.

During operation of the magnetic sensors in a magnetic field, the output of each magnetic distortion sensor can be used to calculate magnitude positions and orientations associated with the mechanical position and orientation of the magnetic distortion sensors relative to one another. In one specific embodiment, for example, the vector sum of the distances are calculated between the magnetic distortion sensors. In response to a distortion in the magnetic field, the perceived location of one (or more) of the magnetic distortion sensors can be displaced from its known/fixed location relative to the other magnetic distortion sensors. As a result, the corresponding vector sum would be correspondingly affected. A change in the vector sum from an initial index value, above a determined threshold, is indicative of a distortion to the generated magnetic field. After determining an initial index-value (where the magnetic field is free of distortions), subsequent magnitude positions and orientations can be correlated timewise. These later magnitude values can vary from the initial index-value due to localized magnetic distortions within the magnetic field, resulting in the erroneous reporting of the location and orientation of the magnetic distortion sensors relative to one another (even though the orientation and position of the magnetic distortion sensors, relative to one another, are fixed). The initial index-value can be compared to subsequent index-values to determine when acceptable levels of magnetic field distortion during a medical procedure are exceeded. The delta value (the change in value between the initial index-value and a subsequent index-value) is associated with distortion related drift in the localization of the catheter.

Additionally, during operation of the impedance patches, the output of at least one impedance location can be used to calculate movement of the impedance location. In response to movement of an impedance patch, the perceived location of one (or more) of the impedance devices can be changed. As a result, a vector of this change in location can be made. A change in the vector, above a determined threshold, can be indicative of a physical movement of a patch. In one embodiment, an acceptable vector value for impedance movement can be determined by the clinician (e.g., a soft threshold value), and/or the processor circuitry (e.g., a hard threshold value). In another embodiment, an acceptable vector value for impedance movement can be preset within the system. In yet other embodiments, the system can suggest one or more acceptable vector values for impedance movement based on various factors for the clinician to select.

Figure 6A:
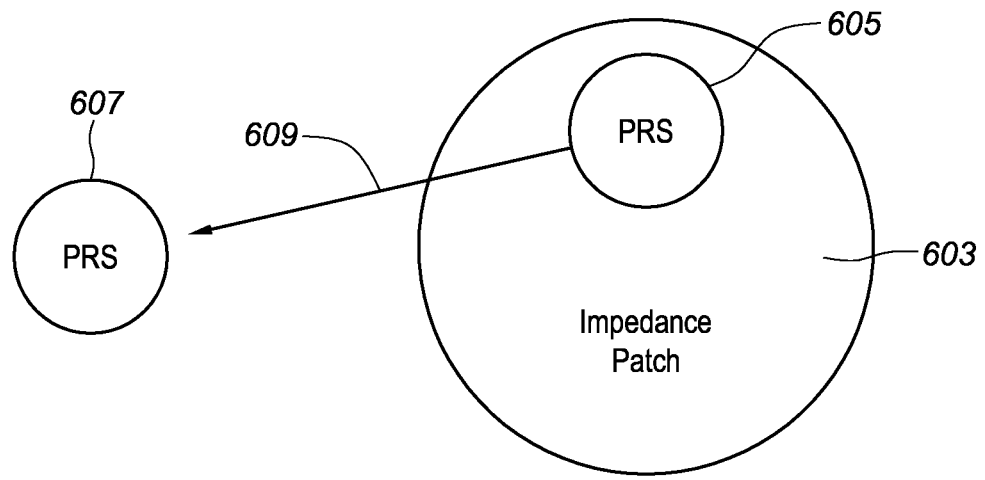
FIGS. 6A-6C are a diagrammatic representation of several embodiments of a system experiencing distortion.
Figure 6B:
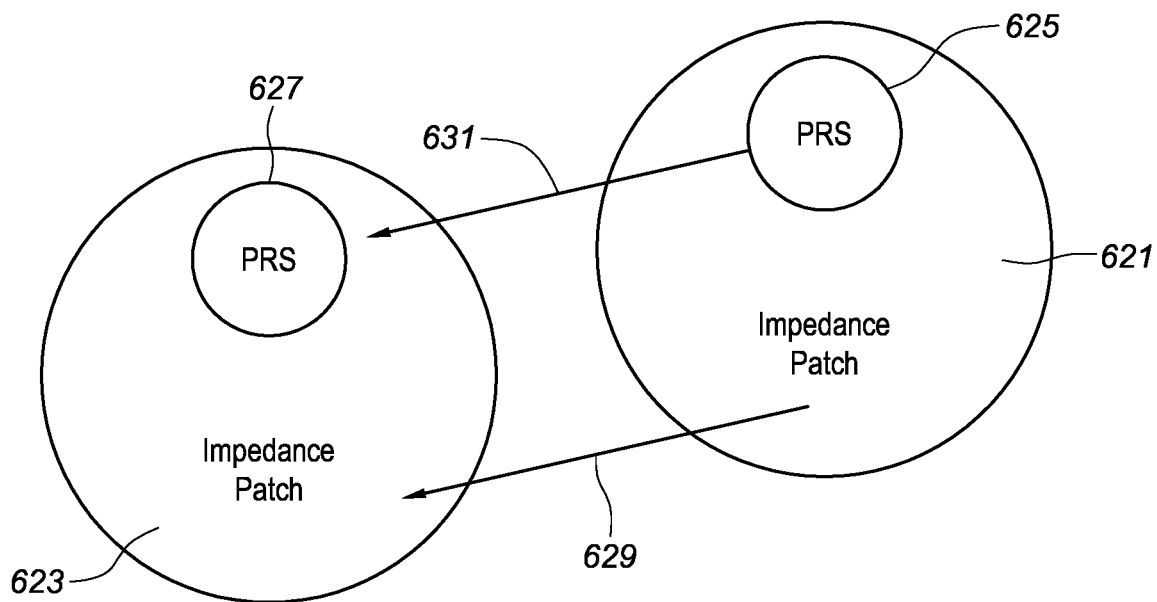
Figure 6C:
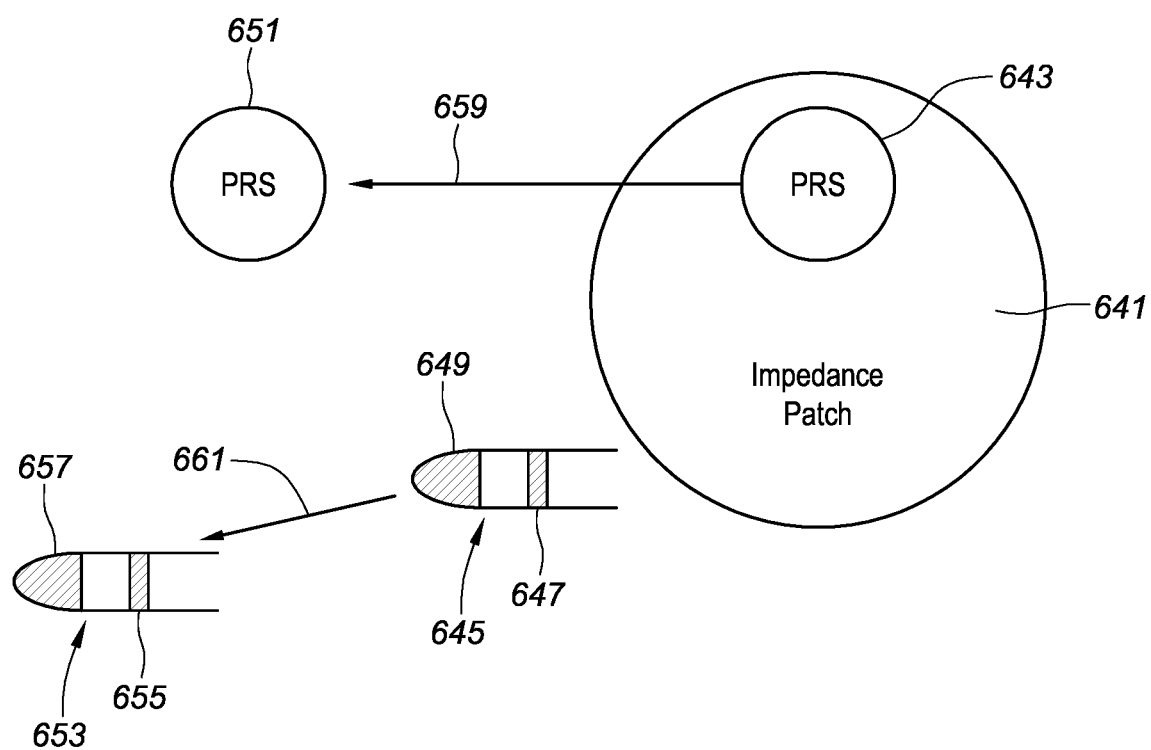

FIGS. 6A-6C illustrate movement detection that can occur under different circumstances. FIG. 6A depicts the movement that would occur when a magnetic field distortion is present. FIG. 6A comprises an impedance patch position 603, a first magnetic sensor position 605, a second magnetic sensor position 607, and a magnetic sensor vector 609. When the system detects a change in position to at least one magnetic sensor and does not detect a change in the patch impedance then a magnetic field distortion can be found. FIG. 6B depicts movement that would occur when patient movement is present. FIG. 6B comprises a first impedance patch position 621, a second impedance path position 623, a first magnetic sensor position 625, a second magnetic sensor position 627, a magnetic sensor vector 631, and an impedance patch vector 629. When the system detects a change in position to at least one magnetic sensor and also detects a change in impedance then the system can determine that patient or other physical movement of the patch and magnetic sensor has occurred. FIG. 6C comprises a first impedance patch position 641, a first magnetic sensor position 643, a first catheter position 645, a first catheter tip electrode position 649, a first catheter ring electrode position 647, a second magnetic sensor position 651, a second catheter position 653, a second catheter tip electrode position 657, a second catheter ring electrode position 655, a magnetic sensor vector 659, and a catheter vector 661. When the system detects a change in position to at least one magnetic sensor and also detects a change in the catheter vector then the system can determine that patient or other physical movement of the catheter electrode and magnetic sensor has occurred. The impedance patch vector and the catheter vector can both influenced by changes in the impedance readings. These vectors can also be referred to as an impedance vector.

In one embodiment, the catheter vector can comprise a vector associated with a movement observed in a single electrode. In another embodiment, the catheter vector can comprise a vector associated with a movement of multiple electrodes present on the catheter. In yet another embodiment, the catheter vector can comprise a vector associated with a movement observed from multiple electrodes on multiple catheters. In one embodiment, the catheter can comprise a reference catheter. The reference catheter can be placed by a physician within the heart in an area where it is unlikely to be dislodged during a procedure. In one embodiment, the reference catheter can be placed within a coronary sinus. In other embodiments, the reference catheter can be disposed within other locations in or around a patient's heart or other organ. In another embodiment, the catheter can comprise a catheter in the atrium, ventricle, or other portion of the hear. In some embodiments, the catheter can comprise a mapping catheter or an ablation catheter.

The mapping system can determine the type of error present in the system using the above information. As stated above, if the system registers a change in position and/or movement of the detected location of the magnetic sensor, but does not register a change in location with the impedance system, then a magnetic distortion is determined to be present. Alternatively, if the system registers a change in position and/or movement of the detected location of the magnetic sensor and also registers a change in location with the impedance system, then a physical movement is determined to be present. By determining the amount of distortion and/or movement present within the system, and the types of movement, the system can determine whether a magnetic distortion or physical movement is present. As described above, in one embodiment, the system can use thresholds to determine if the amount of movement perceived by the system is large enough to detect. If a magnetic distortion or physical movement is detected, in one embodiment, the system can alert a physician or doctor to this error state. This information can be conveyed to the clinician through the use of audible, visual, haptic, or other sensory feedback. In another embodiment, the system can notify the physician and the physician can physically rectify the movement. In another embodiment, the system can notify the physician and the system can algorithmically rectify any shift or movement that has occurred within the system.

A mapping system as described herein can detect movements occurring at a millisecond time length. In one embodiment, the mapping system can review changes to values at these millisecond time lengths and alert a physician if movement and/or distortion occurs. In other embodiments, the mapping system can look for changes on a single second to multi-second time lengths. Additionally, the mapping system may detect normal, rhythmic movement, such as respiration of a patient. In some embodiments, the amount of movement of a location during patient respiration can be greater than a threshold. In some embodiments, the system can be configured to compensate for this respiration movement. In one embodiment, the system can use compensation algorithms to compensate for movement during respiration.

In other embodiments, the system can disregard cyclical movement, such as respiration, and instead review the data for permanent changes. In one embodiment, the system can review time periods of under a second for permanent change. In another embodiment, the system can review time periods of 1-5 seconds for permanent change. In yet another embodiment, the system can review time periods of 1-10 seconds for a permanent change.

In response, the mapping system can ignore the location data from the magnetic field-based portion of the system, or correct for the distortion. For example, data from one or more of the magnetic distortion sensors can be used to determine a variance between actual locations (based on the known/fixed position of the magnetic distortion sensor within the system) and perceived locations (those determined based on the received magnetic fields at the magnetic distortion sensor and post-processing). The determined variance can be indicative of magnetic distortion or physical movement throughout the magnetic field due to egress of ferrous/metallic objects into the magnetic field or a physical movement of the sensor. Based on the variance at each of the magnetic distortion sensor locations, a transform can be computed to correct for the distortion or movement at all locations within the magnetic field, including the magnetic distortion or movement experienced by the medical device being magnetically localized. In other embodiments, the hybrid magnetic and impedance tracking system can automatically change location sensing of a medical device to only rely on the impedance location sensing when the system determines a magnetic distortion is affecting the system. In other embodiments, the hybrid magnetic and impedance tracking system can signal to the user that a magnetic distortion is present and the user can then select the option to proceed by only sensing impedance location data of a medical device. In some embodiments, this operation can be called impedance mode. In various embodiments, the impedance location sensing mode can continue until the magnetic distortion is no longer affecting the system, at which point, the system can automatically switch back to using the magnetic tracking system the same as before the magnetic distortion was present. In other embodiments, the impedance location sensing mode can continue until the magnetic distortion is no longer affecting the system, at which point, the system can signal to a user whether they want to switch back to using the magnetic tracking system the same as before the magnetic distortion was present.

In the embodiments described herein, the magnetic distortion sensors can be generally centered about the portion of the patient's body where the medical device localization is to take place. For example, in a cardiac-related operation, the magnetic distortion sensors can be positioned in close proximity to the patient's heart to improve detection of magnetic distortions affecting the medical device therein.

It should be noted that the features illustrated in the drawings are not necessarily drawn to scale, and features of one embodiment can be employed with other embodiments as the skilled artisan would recognize, even if not explicitly stated herein. Descriptions of well-known components and processing techniques can be omitted so as to not unnecessarily obscure the embodiments of the disclosure. The examples used herein are intended merely to facilitate an understanding of ways in which the disclosure can be practiced and to further enable those of skill in the art to practice the embodiments of the disclosure. Accordingly, the examples and embodiments herein should not be construed as limiting the scope of the disclosure.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, can be described in a sequential order, such processes, methods and algorithms can be configured to work in alternate orders. In other words, any sequence or order of steps that can be described does not necessarily indicate a requirement that the steps be performed in that order. The steps of the processes, methods or algorithms described herein can be performed in any order practical. Further, some steps can be performed simultaneously.

When a single device or article is described herein, it will be readily apparent that more than one device or article can be used in place of a single device or article. Similarly, where more than one device or article is described herein, it will be readily apparent that a single device or article can be used in place of the more than one device or article. The functionality or the features of a device can be alternatively embodied by one or more other devices which are not explicitly described as having such functionality or features.

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments can be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein can be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics can be combined in any suitable manner in one or more embodiments. Thus, the particular features, structures, or characteristics illustrated or described in connection with one embodiment can be combined, in whole or in part, with the features, structures, or characteristics of one or more other embodiments without limitation given that such combination is not illogical or non-functional.

It will be appreciated that the terms "proximal" and "distal" can be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" can be used herein with respect to the illustrated embodiments. However, surgical instruments can be used in many orientations and positions, and these terms are not intended to be limiting and absolute.

What is claimed is:

1. A system for differentiating between magnetic field distortion and physical movement in a hybrid magnetic and impedance tracking system for navigating a medical device within a patient, the system comprising:
    an impedance localization system comprising a first drive patch and a second drive patch configured to be coupled to an external surface of the patient's body, the first and second drive patches configured to generate an electrical field within the body for locating an electrode on the medical device;
    a magnetic localization system configured to generate a magnetic field;
    a magnetic sensor coupled to one of the first and second drive patches and configured to receive signals from the magnetic localization system; and
    an electronic control unit configured to receive drive patch location data from the impedance localization system and magnetic sensor location data from the magnetic localization system, wherein the electronic control circuit is configured to detect a location change of the magnetic sensor and use the drive patch location data and magnetic sensor location data to determine whether the detected location change of the magnetic sensor is caused by a magnetic field distortion or a physical movement of the magnetic sensor.

2. The system according to claim 1, wherein the magnetic sensor further comprises outputting a reference signal, the reference signal establishing an origin of the coordinate system.

3. The system according to claim 1, wherein the magnetic sensor comprises a plurality of sensor coils positioned at fixed distances and orientations relative to one another, each of the sensor coils configured and arranged to sense the magnetic field co-planar with the orientation of the sensor coil and output an electrical signal indicative of a sensed magnetic field.

4. The system according to claim 1, wherein the electronic control unit determines a first magnetic sensor position, a second magnetic sensor position, and a magnetic field distortion sensor vector when determining whether a magnetic field distortion or physical movement of the magnetic sensor has occurred.

5. The system according to claim 1, wherein the electronic control unit determines an impedance vector when determining whether a magnetic field distortion or physical movement of the magnetic sensor has occurred.

6. The system according to claim 1, wherein the electronic control unit determines an original magnetic sensor position, a measured magnetic sensor position, an original drive patch position, and a measured drive patch position when determining whether a magnetic field distortion has occurred.

7. The system according to claim 1, wherein the electronic control unit determines an original magnetic sensor position, a measured sensor position, an original drive patch position, and a measured drive patch position when determining whether a physical movement of the magnetic sensor has occurred.

8. The system according to claim 1, wherein the magnetic sensor comprises a first magnetic sensor and wherein the system further comprises a third drive patch and a second magnetic sensor coupled to the third drive patch.

9. The system according to claim 1, wherein the impedance localization system is configured to determine a measured location of the medical device and wherein the electronic control unit is configured to correct the measured location of the medical device due to the magnetic field distortion or the physical movement of the magnetic sensor.

10. The system according to claim 1, wherein the electronic control unit is configured to output a location of the electrode on the medical device while disregarding information from the magnetic localization system when a magnetic field distortion is detected.

11. A system for differentiating between magnetic field distortion and physical movement in a hybrid magnetic and impedance tracking system for navigating a medical device within a patient, the system comprising:
    a magnetic localization system configured to generate a magnetic field;
    a magnetic sensor comprising a first sensor coil, a second sensor coil oriented orthogonal to the first sensor coil, and a third sensor coil oriented orthogonal to the first and second sensor coils and configured to receive signals from the magnetic localization system;
    a plurality of impedance patches configured to generate an electric field within the patient's body for locating an electrode on a medical device; and
    an electronic control unit configured to receive information from the magnetic sensor and the plurality of impedance patches, wherein the electronic control unit is configured to determine a magnetic sensor vector and an impedance vector, wherein the electronic control circuit is configured to detect a location change of the magnetic sensor and use the magnetic sensor vector and the impedance vector to determine whether the detected location change is caused by a magnetic field distortion or a physical movement of the magnetic sensor, and wherein the electronic control unit is configured to initiate a correction algorithm, wherein the correction algorithm is configured to correct a change in a position of the medical device based on the magnetic field distortion or by the physical movement of the magnetic sensor.

12. The system according to claim 11, wherein the first, second, and third sensor coils are configured and arranged to receive energy indicative of a magnetic field strength and a magnetic field orientation substantially coaxial with the receiving sensor coil.

13. The system according to claim 11, wherein the magnetic sensor is coupled to one of the plurality of impedance patches.

14. The system according to claim 11, wherein the electronic control unit is configured to send out a notification when a threshold value of magnetic field distortion or physical movement of the magnetic sensor has occurred.

15. A method for differentiating between magnetic field distortion and physical movement in a hybrid magnetic and impedance tracking system for navigating a medical device within a patient, the method comprising:
   receiving a first set of one or more signals from a magnetic sensor indicative of a magnetic field sensed by each of a plurality of sensor coils within the magnetic sensor at a first time;
   receiving a first set of one or more signals from an impedance sensor indicative of a position within a coordinate system;
   receiving a second set of one or more signals from the magnetic sensor indicative of the magnetic field sensed by each of the sensor coils at a second time;
   receiving a second set of one or more signals from the impedance sensor indicative of a position within the coordinate system;
   determining a magnetic sensor vector;
   determining an impedance vector;
   detecting a location change of the magnetic sensor;
   comparing the magnetic sensor vector to a first threshold and the impedance vector to a second threshold to determine whether the detected location change of the magnetic sensor is caused by a magnetic field distortion or a physical movement of the magnetic sensor has occurred;
   wherein the detected location change is caused by a magnetic field distortion if the magnetic sensor vector is over the first threshold and the impedance vector is under the second threshold; and
   wherein the detected location change is caused by a physical movement of the magnetic sensor if the magnetic sensor vector is over the first threshold and the impedance vector is over the second threshold.

16. The method according to claim 15, further comprising notifying a physician when a magnetic field distortion or a physical movement of the magnetic sensor has occurred.

17. The method according to claim 15, wherein the impedance sensor comprises a patch.

18. The method according to claim 15, wherein the magnetic sensor is coupled to the impedance sensor.

19. The method according to claim 15, wherein the impedance sensor comprises an electrode on a medical device.

20. The method according to claim 19, further comprising running a correction algorithm, wherein the correction algorithm is configured to correct a change in a position of the medical device based on the magnetic field distortion or by the physical movement of the magnetic sensor.

* * * * *